US010663456B2

(12) United States Patent
Tani et al.

(10) Patent No.: US 10,663,456 B2
(45) Date of Patent: May 26, 2020

(54) METHOD FOR MEASURING IN VIVO INHIBITION OF INTRACELLULAR RNASE

(71) Applicant: NATIONAL INSTITUTE OF ADVANCED INDUSTRIAL SCIENCE AND TECHNOLOGY, Tokyo (JP)

(72) Inventors: Hidenori Tani, Ibaraki (JP); Masaki Torimura, Ibaraki (JP); Hiroaki Sato, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 15/746,570

(22) PCT Filed: Jul. 6, 2016

(86) PCT No.: PCT/JP2016/070036
§ 371 (c)(1),
(2) Date: Jan. 22, 2018

(87) PCT Pub. No.: WO2017/018145
PCT Pub. Date: Feb. 2, 2017

(65) Prior Publication Data
US 2018/0217128 A1 Aug. 2, 2018

(30) Foreign Application Priority Data

Jul. 24, 2015 (JP) .................... 2015-147125

(51) Int. Cl.
| C07H 21/04 | (2006.01) |
| G01N 33/50 | (2006.01) |
| G01N 33/542 | (2006.01) |
| C12Q 1/34 | (2006.01) |
| G01N 33/53 | (2006.01) |
| C12Q 1/68 | (2018.01) |
| C12N 15/09 | (2006.01) |
| G01N 33/58 | (2006.01) |

(52) U.S. Cl.
CPC ......... *G01N 33/5014* (2013.01); *C12N 15/09* (2013.01); *C12Q 1/34* (2013.01); *C12Q 1/68* (2013.01); *G01N 33/53* (2013.01); *G01N 33/5308* (2013.01); *G01N 33/542* (2013.01); *G01N 33/582* (2013.01)

(58) Field of Classification Search
None
See application file for complete search history.

(56) References Cited

U.S. PATENT DOCUMENTS 6,063,587 A 5/2000 Ishiyama et al.
2003/0108930 A1 6/2003 Ishiguro et al.

FOREIGN PATENT DOCUMENTS

| JP | 2592436 | 12/1996 |
| JP | 2757348 | 3/1998 |
| JP | 2003-116543 | 4/2003 |
| JP | 2004-290093 | 10/2004 |
| JP | 2010-178716 | 8/2010 |
| JP | 2012-10667 | 1/2012 |
| JP | 2013-99277 | 5/2013 |
| WO | 2013/067498 | 5/2013 |

OTHER PUBLICATIONS

Tani, Hidenori, et al. "Real-time monitoring of RNA helicase activity using fluorescence resonance energy transfer in vitro." Biochemical and biophysical research communications 393.1 (2010): 131-136.*
Extended European Search Report dated Nov. 29, 2018 in corresponding European patent application No. 16830250.3.
Huang et al., "Site-Specific RNase A Activity Was Dramatically Reduced in Serum from Multiple Types of Cancer Patients", PLOS ONE, 2014, vol. 9, No. 5, p. e96490, XP055524960, 8 pages.
Järve et al., "Surveillance of siRNA integrity by FRET imaging", Nucleic Acids Research, 2007, vol. 35, No. 18, p. e124, XP055525392, 13 pages.
Su et al., "Simultaneous Fluorescence Imaging of the Activities of DNases and 3' Exonucleases in Living Cells with Chimeric Oligonucleotide Probes", Analytical Chemistry, 2013, vol. 85, No. 20, pp. 9939-9946.
International Search Report dated Sep. 27, 2016 in International (PCT) Application No. PCT/JP2016/070036.

(Continued)

*Primary Examiner* — Kimberly Chong
(74) *Attorney, Agent, or Firm* — Wenderoth, Lind & Ponack, L.L.P.

(57) ABSTRACT

The present invention provides means for evaluating harmfulness of a chemical substance before occurrence of cell death, that is, more quickly and sensitively compared to conventional methods wherein the remaining viable cell count is determined using a reductive coloring reagent after a period of time required for occurrence of cell death due to the chemical substance. A double-stranded RNA probe comprising an RNA strand labeled with a fluorescent dye A that emits fluorescence, and an RNA strand labeled with a fluorescent dye B that quenches emission from a fluorescent dye in the vicinity thereof, wherein the fluorescence is quenched in a double-stranded state due to occurrence of fluorescence resonance energy transfer (FRET) between the two kinds of fluorescent dyes. When the probe is introduced into a cell and the cell is in a normal state, the double-stranded RNA is quickly degraded by activity of intracellular ribonuclease to cause cancellation of the FRET state, allowing fluorescence emission of the fluorescent dye A. On the other hand, in cases where the cell is harmfully influenced, activity of intracellular ribonuclease is suppressed, so that the double-stranded RNA remains undegraded, and the fluorescent dye A remains quenched due to the influence of the fluorescent dye B. By detecting a decrease in the degradation rate of intracellular RNA based on this principle, harmfulness of a chemical substance can be quickly and sensitively evaluated before occurrence of cell death.

4 Claims, 7 Drawing Sheets

Specification includes a Sequence Listing.

(56) References Cited

OTHER PUBLICATIONS

Vistica et al., "Tetrazolium-based Assays for Cellular Viability: A Critical Examination of Selected Parameters Affecting Formazan Production", Cancer Research, vol. 51, May 15, 1991, pp. 2515-2520.

Roehm et al., "An improved colorimetric assay for cell proliferation and viability utilizing the tetrazolium salt XTT", Journal of Immunological Methods, vol. 142, 1991, pp. 257-265.

Ishiyama et al., "A highly water-soluble disulfonated tetrazolium salt as a chromogenic indicator for NADH as well as cell viability", Talanta, vol. 44, 1997, pp. 1299-1305.

Marras et al., "Efficiencies of Fluorescence resonance energy transfer and contact-mediated quenching in oligonucleotide probes", Nucleic Acids Research, vol. 30, No. 21, 2002, e122, pp. 1-8.

Tani et al., "Genome-wide determination of RNA stability reveals hundreds of short-lived noncoding transcripts in mammals", Genome Research, vol. 22, pp. 947-956, 2012.

\* cited by examiner

SEQUENCE LISTING

```
<160> NUMBER OF SEQ ID NOS: 2

<210> SEQ ID NO 1
<211> LENGTH: 23
<212> TYPE: RNA
<213> ORGANISM: artificial sequence
<220> FEATURE:
<223> OTHER INFORMATION: probe

<400> SEQUENCE: 1
cauaauccac cucccacuau ucc                                        23

<210> SEQ ID NO 2
<211> LENGTH: 23
<212> TYPE: RNA
<213> ORGANISM: artificial sequence
<220> FEATURE:
<223> OTHER INFORMATION: probe

<400> SEQUENCE: 2
ggaauagugg gagguggauu aug                                        23
```

METHOD FOR MEASURING IN VIVO INHIBITION OF INTRACELLULAR RNASE

TECHNICAL FIELD

The present invention relates to a technique in the field of life science and the field of environmental analysis, in particular, to a technique for biological assessment of harmful chemical substances using cultured cells.

BACKGROUND ART

As methods for biological assessment (bioassay) of chemical substances, especially as methods for evaluation of harmfulness of chemical substances, methods based on determination of the viable cell count using cultured cells such as mammalian cells have been established as alternatives to animal experiments using mice, rats, or the like. In methods commonly employed in the previous studies, the viable cell count is determined by measurement of the absorbance, and a decrease in the number of the cells is measured. For example, the MTT method, which uses a reductive coloring reagent and mitochondrial dehydrogenase activity in live cells (Non-patent Document 1); and the XTT method (Non-patent Document 2) and the WST method (Patent Document 1, Patent Document 2, Non-patent Document 3), which are colorimetric methods based on measurement of enzymatic activity that causes reduction into MTT-like dyes; are widely used at present from the viewpoint of safety of measurement, high reproducibility, and the like. In particular, in the WST method; water-soluble formazan is produced after the addition of the reagent, so that the method allows sensitive and simple determination of the viable cell count, and stability after the preparation of the aqueous solution is high. However, these methods have a drawback in that a long time is required for allowing the cultured cells to respond to harmfulness of the chemical substance, finally showing a phenotype causing cell death.

PRIOR ART DOCUMENTS

Patent Documents

Patent Document 1: JP 2592436 B
Patent Document 2: JP 2757348 B
Patent Document 3: JP 2012-10667 A

Non-Patent Documents

Non-patent Document 1: Vistica, D. T. et al., Cancer Res., 51, 2515-2520, 1991
Non-patent Document 2: Roehm, N. W. et al., J. Immunol. Methods, 142, 257-265, 1991
Non-patent Document 3: Ishiyama, M. et al., Talanta, 44, 1299-1305, 1997
Non-patent Document 4: Marras, S. A. E. et al., Nucleic Acids Res., 30, e122, 2002
Non-patent Document 5: Tani, H. et al., Genome Res., 22, 947-956, 2012

DISCLOSURE OF THE INVENTION

Problems to be Solved by the Invention

An object of the present invention is to solve the above-described problems of conventional techniques, and the present invention aims to provide means for evaluating harmfulness of a chemical substance before occurrence of cell death, that is, more quickly and sensitively compared to conventional methods that are based on determination of the viable cell count using a reductive coloring reagent after a period of time required for occurrence of cell death due to the chemical substance.

Means for Solving the Problems

As a result of intensive study to solve the problems described above, the present inventors discovered that harmfulness of a chemical substance to cultured cells can be evaluated by measuring the degradation rate of intracellular RNA, and that, by preparing an RNA probe labeled with a fluorescent dye such that fluorescence emission occurs when the cells are normal and intracellular RNA is rapidly degraded while the fluorescence emission does not occur when the cells are harmfully influenced and intracellular RNA is not degraded, introducing the prepared RNA probe into the cells, and detecting a decrease in the degradation rate of intracellular RNA, harmfulness of the chemical substance can be evaluated before occurrence of cell death, that is, more quickly and sensitively compared to conventional methods, thereby solving the problems described above.

That is, the present inventors designed and prepared a double-stranded RNA comprising an RNA strand labeled with a fluorescent dye A that emits fluorescence, and an RNA strand labeled with a fluorescent dye B that quenches emission from a fluorescent dye in the vicinity thereof. When the double-stranded RNA is in a double-stranded state, the fluorescence is in a quenched state due to occurrence of fluorescence resonance energy transfer (FRET) (Non-patent Document 4) between the two kinds of fluorescent dyes. The present inventors discovered that, when the double-stranded RNA is introduced into a cell, in cases where the cell is in a normal state, the double-stranded RNA is quickly degraded by activity of intracellular ribonuclease to cause cancellation of the FRET state, allowing fluorescence emission of the fluorescent dye A, whereas in cases where the cell is harmfully influenced, activity of intracellular ribonuclease is suppressed, so that the double-stranded RNA remains undegraded, and the fluorescent dye A remains quenched due to the influence of the fluorescent dye B, and thereby completed the present invention (see the conceptual diagram for the present invention shown in FIG. 1).

In a conventional reported method for measuring the degradation rate of such intracellular RNA, cells are cultured in a medium containing a halogenated uridine to allow incorporation of the halogenated uridine into intracellular RNA while obtaining cell samples over time, and then halogenated-uridine-containing RNA is isolated using an anti-halogenated uridine antibody (Patent Document 3, Non-patent Document 5). However, this method takes 24 hours for the incorporation of halogenated uridine, and further includes the process of obtaining samples over time, extracting RNA from the cells, and isolating the halogenated-uridine-containing RNA. Therefore, a long time is required for the detection of a decrease in the degradation rate of intracellular RNA, and a complicated operation is necessary.

In contrast, the method of the present invention allows detection, in a very short length of time of about several hours, of a decrease in the degradation rate of intracellular RNA caused by a harmful substance as shown in the Examples shown below. Thus, harmfulness of the chemical substance can be quickly evaluated.

That is, the present application provides the following inventions.

<1> A double-stranded RNA probe comprising an RNA strand labeled with a fluorescent dye A that emits fluorescence, and an RNA strand labeled with a fluorescent dye B that quenches emission from a fluorescent dye in the vicinity thereof, wherein the fluorescence is quenched in a double-stranded state due to occurrence of fluorescence resonance energy transfer (FRET) between the two kinds of fluorescent dyes.

<2> A method for evaluating activity of intracellular ribonuclease, the method comprising:

introducing the probe recited in <1> into a cell; and detecting a decrease in the degradation rate of intracellular RNA by measuring fluorescence emission, which detection utilizes the principle that, in cases where double-stranded RNA is degraded by activity of intracellular ribonuclease, the FRET state is canceled, allowing fluorescence emission of the fluorescent dye A, while in cases where activity of intracellular ribonuclease is suppressed, double-stranded RNA remains undegraded, making the fluorescent dye A remain quenched due to influence of the fluorescent dye B.

<3> A method for evaluating harmfulness of a chemical substance to a cell, the method comprising:

introducing, into a cell, the compound to be evaluated for its harmfulness to the cell, and the probe recited in <1>; and detecting a decrease in the degradation rate of intracellular RNA by measuring fluorescence emission, which detection utilizes the principle that, in cases where double-stranded RNA is degraded by activity of intracellular ribonuclease, the FRET state is canceled, allowing fluorescence emission of the fluorescent dye A, while in cases where activity of intracellular ribonuclease is suppressed, double-stranded RNA remains undegraded, making the fluorescent dye A remain quenched due to influence of the fluorescent dye B.

<4> The method according to <3>, wherein the chemical substance is hydrogen peroxide.

<5> The method according to <3>, wherein the chemical substance is Cisplatin.

<6> The method according to <3>, wherein the chemical substance is Mercury II Chloride.

Effect of the Invention

According to the present invention, unlike the above-mentioned conventional techniques, harmfulness of a chemical substance can be quickly and sensitively evaluated by measuring the activity of intracellular ribonuclease using a double-stranded RNA labeled with fluorescent dyes, without requiring the time until occurrence of cell death due to the harmfulness of the chemical substance.

In conventional techniques, only end-point measurement is possible since the evaluation of harmfulness of a chemical substance is carried out by determination of the viable cell count. Therefore, for investigation of changes over time, cell lines in a number sufficient for covering the necessary time points must be provided. In contrast, in the method of the present invention, real-time measurement is possible, so that the number of cells to be provided can be reduced.

EMBODIMENTS FOR CARRYING OUT THE INVENTION

The present invention is described below more concretely by way of Examples. However, the present invention is not limited to these Examples.

EXAMPLES

Example 1

Figure 1:
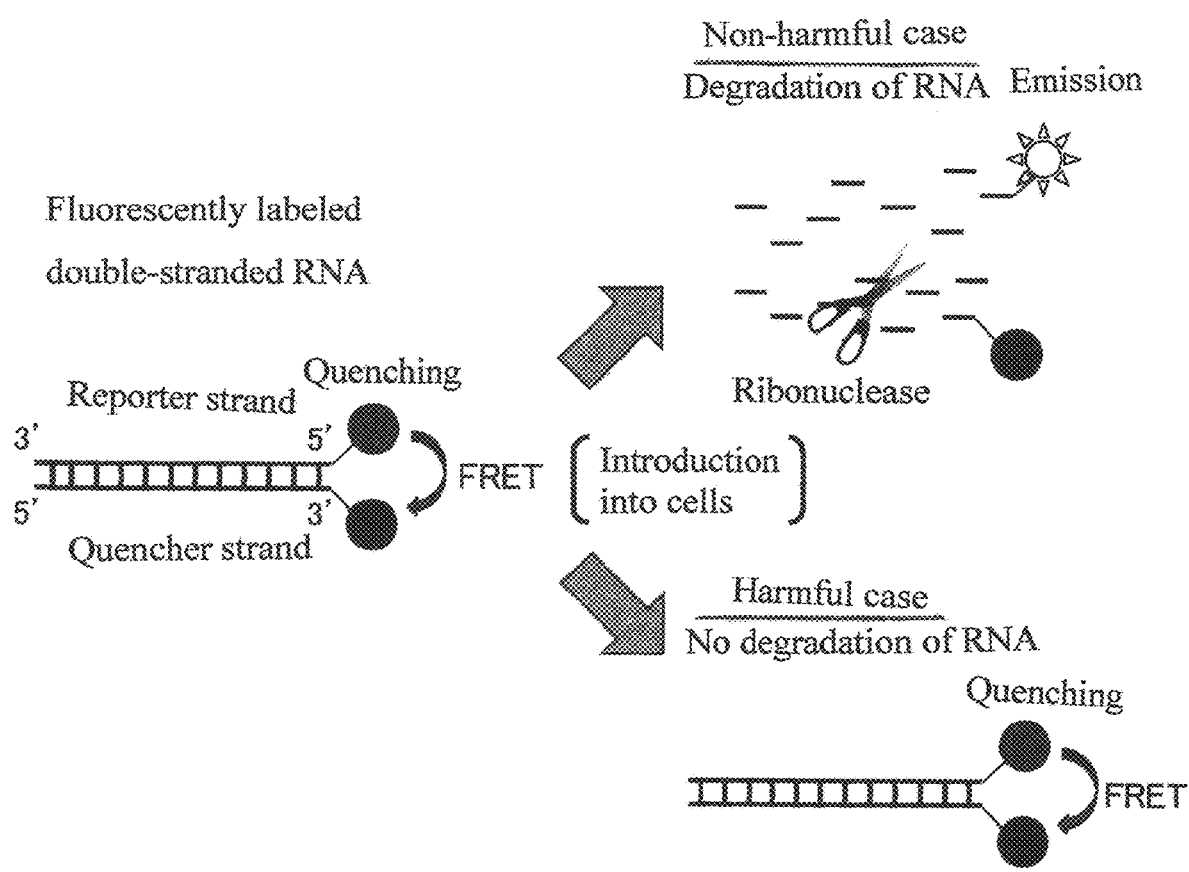
FIG. 1 is a conceptual diagram for the present invention.

Observation of Quenching of Fluorescently Labeled Double-Stranded RNA by FRET, and of Production of Fluorescence Due to RNA Strand Degradation by Ribonuclease This experiment was carried out for confirming quenching of the fluorescently labeled double-stranded RNA by FRET, and for studying whether an increase in the fluorescence value occurs by ribonuclease (FIG. 1).

Figure 2:
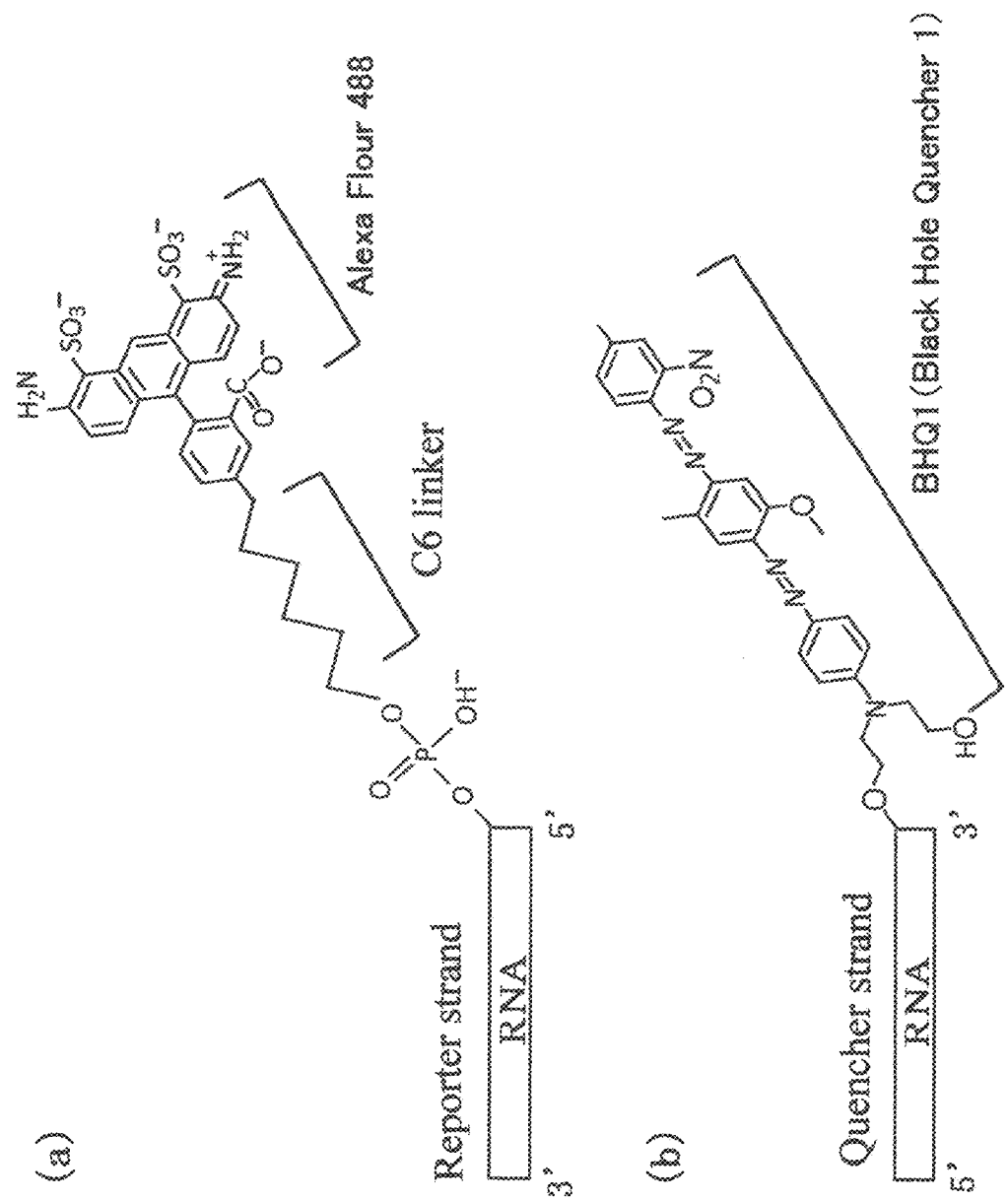
FIG. 2 is a diagram illustrating a specific example of the fluorescently labeled double-stranded RNA to be used in the present invention.

First, FRET-Alexa-RNA: 5'-(Alexa Flour 488)-CAUAAUCCACCUCCCACUAUUCC-3' (SEQ ID NO: 1) as a reporter strand, and FRET-BHQ1-RNA: (5'-GGAAUAGUGGGAGGUGGAUUAUG-(BHQ1)-3' (SEQ ID NO:2) as a quencher strand were provided. The base at the 5' end of the reporter strand is labeled with Alexa Flour 488 through a C6 linker, and the base at the 3' end of the quencher strand is labeled with BHQ1 (Black Hole Quencher 1) without use of a linker (FIG. 2).

The reporter strand and the quencher strand were mixed at a ratio of 1:2 (molar ratio) in a solution of 50 mM HEPES, 500 mM KCl, and 25 mM $MgCl_2$, and the resulting solution was incubated at 99° C. for 5 minutes, at 65° C. for 30 minutes, and then at 25° C. for 30 minutes to prepare a double-stranded RNA. Subsequently, a reaction liquid containing 200 nM double-stranded RNA in Opti-MEM (Life Technologies) (50 µL) was provided, and fluorescence was measured at 519 nm with excitation at 488 nm using a Microplate Reader SH-9000 (Corona Electric) (the result at Hour 0).

Thereafter, 0.4 mg/ml Ribonuclease (DNase free) Solution (ribonuclease; RNase) (Nippon Gene) was added to the reaction liquid, and the resulting mixture was incubated at room temperature for 1 hour, followed by measurement of fluorescence at 519 nm with excitation at 488 nm using a Microplate Reader SH-9000 (Corona Electric) (the result at Hour 1). The experiment was carried out for n=3.

Figure 3:
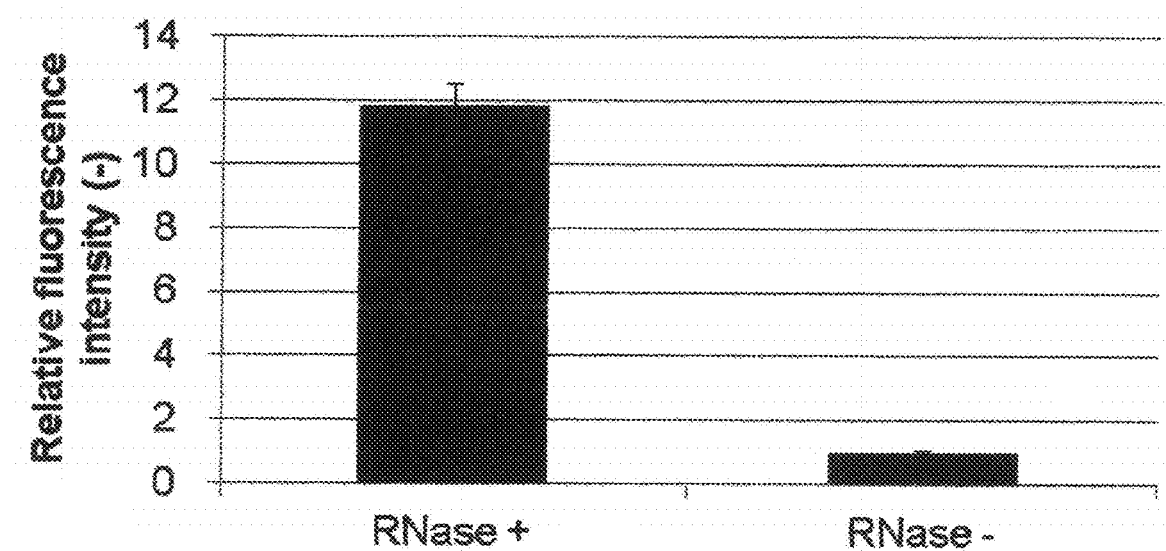
FIG. 3 is a diagram illustrating the result of an experiment for observation of quenching of the fluorescently labeled double-stranded RNA of the present invention by FRET, and of production of fluorescence due to RNA strand degradation by ribonuclease.

The result obtained by dividing the fluorescence value at Hour 1 by the fluorescence value at Hour 0 is shown in FIG. 3. From the result shown in FIG. 3, it could be confirmed that the fluorescence intensity obviously increased by the addition of RNase compared to the case where no RNase was added. This result indicates that the fluorescently labeled double-stranded RNA is quenched by FRET, and that degradation of the RNA strands by the ribonuclease causes fluorescence emission.

Example 2

Influence of Hydrogen Peroxide on Fluorescently Labeled Double-Stranded RNA and Ribonuclease In this experiment, how hydrogen peroxide influences the fluorescently labeled double-stranded RNA and a Ribonuclease (DNase free) Solution (ribonuclease; RNase) (Nippon Gene) was investigated.

A reaction liquid containing 200 nM double-stranded RNA in Opti-MEM (Life Technologies) (50 µL) was provided, and fluorescence was measured at 519 nm with excitation at 488 nm using a Microplate Reader SH-9000 (Corona Electric) (the result at Hour 0). Thereafter, systems in each of which hydrogen peroxide was added at 0 or 100 µM, and Ribonuclease (DNase free) Solution (ribonuclease; RNase) (Nippon Gene) was added at 0 or 0.4 mg/ml, were provided, and each system was incubated at room temperature for 1, 2, or 4 hours, followed by measurement of fluorescence at 519 nm with excitation at 488 nm using a Microplate Reader SH-9000 (the result at Hour 1, 2, or 4). The experiment was carried out for n=3.

Figure 4:
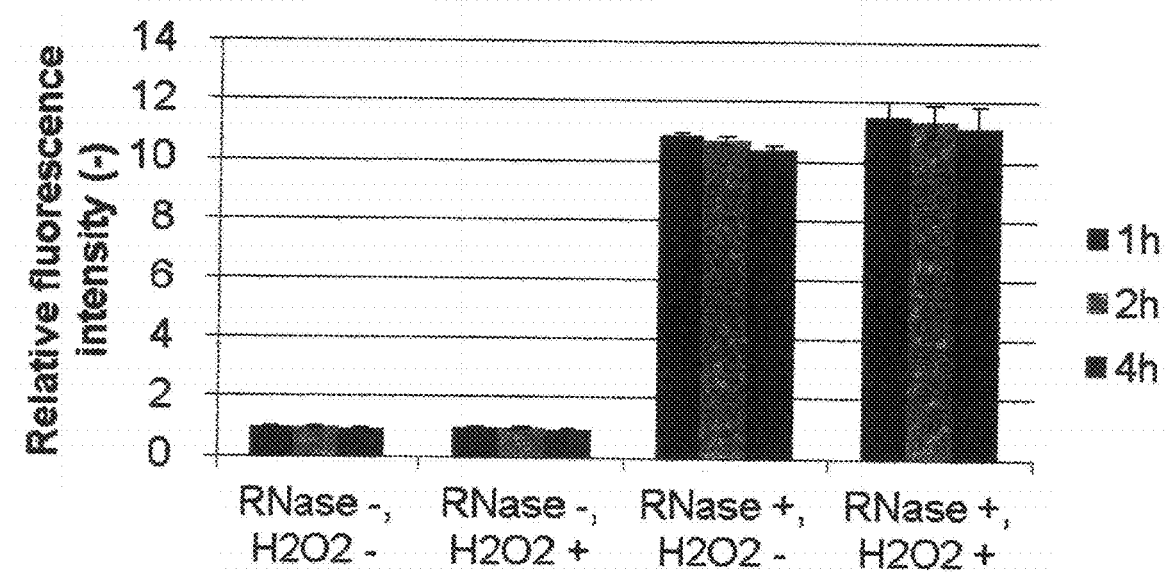
FIG. 4 is a diagram illustrating that hydrogen peroxide does not influence the fluorescently labeled double-stranded RNA of the present invention and ribonuclease in the outside of the cell.

The result obtained by dividing the fluorescence value at Hour 1, 2, or 4 by the fluorescence value at Hour 0 is shown in FIG. 4. As can be seen from the result shown in FIG. 4, the fluorescence value of the system that does not contain RNase but contains hydrogen peroxide was almost the same as that of the system that contains neither RNase nor hydrogen peroxide, and the fluorescence value of the system that contains both RNase and hydrogen peroxide was almost the same as that of the system that contains RNase but not hydrogen peroxide.

This result indicates that hydrogen peroxide influences neither the fluorescence value of the RNA FRET Probe nor the RNase activity.

Example 3

Evaluation of Harmfulness of Hydrogen Peroxide to Cells Using Fluorescently Labeled Double-Stranded RNA In this experiment, hydrogen peroxide was used as a harmful chemical substance to cells, and a fluorescently labeled double-stranded RNA was introduced into mammalian cells. A study was carried out to see whether evaluation of harmfulness of the chemical substance to the cells is possible based on the fluorescence value.

As reaction liquids, systems each containing 50 µL of Opti-MEM (Life Technologies), 1 µL of Lipofectamine 2000 (Life Technologies), 200 nM double-stranded RNA (the same RNA as in Example 1), and 0, 0.01, 1, or 100 µM hydrogen peroxide (Wako) were provided. After mixing, each reaction liquid was incubated at room temperature for 20 minutes, and then added to HEK 293 cells ($2\times10^5$ cells/ml in 96 well plate), which are human cells. From Hour 0 to Hour 8, fluorescence was measured at 519 nm with excitation at 488 nm using a Microplate Reader SH-9000 (Corona Electric) at one-hour intervals. The experiment was carried out for n=3.

Figure 5:
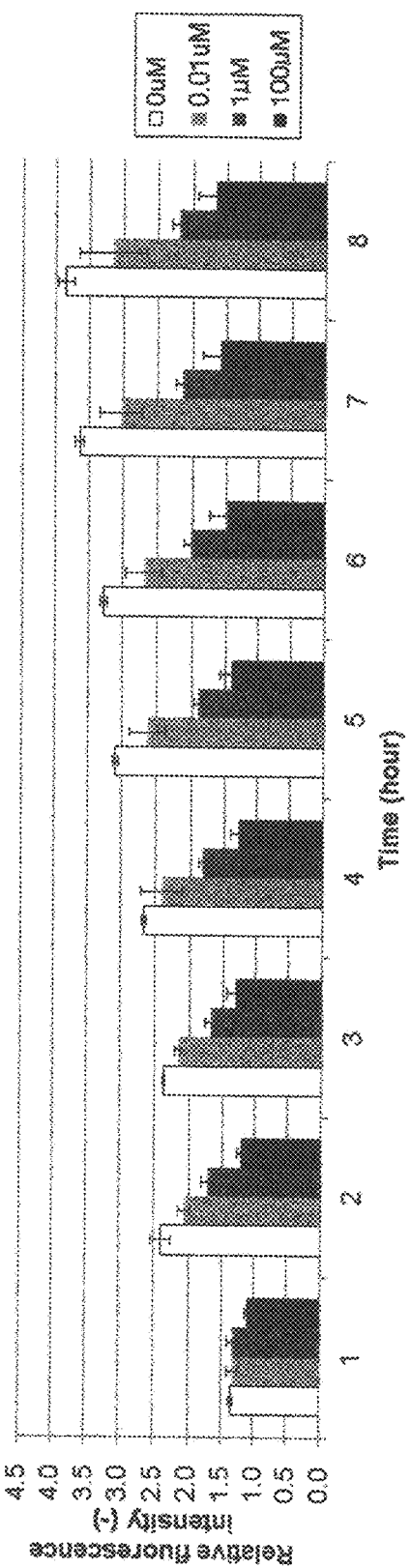
FIG. 5 is a diagram illustrating the result of evaluation of harmfulness of hydrogen peroxide to cells, which evaluation was carried out using the fluorescently labeled double-stranded RNA of the present invention.

The result obtained by dividing the fluorescence values at Hours 1 to 8 by the fluorescence value at Hour 0 is shown in FIG. 5. According to the result shown in FIG. 5, it was found that, while the fluorescence value increases with time in the system to which hydrogen peroxide was not added (0 µM), the increase in the fluorescence value is suppressed in the systems to which hydrogen peroxide was added, and that the suppression is dependent on the hydrogen peroxide concentration. Further, it was found that the changes can be clearly observed in two hours in these systems.

As shown above in Example 2, RNase activity is not influenced by hydrogen peroxide in in vitro cell-free experiments. Thus, it can be seen that the apparent decrease in the RNase activity caused by hydrogen peroxide in the intracellular experiment is due to influence of hydrogen peroxide on the cells that causes the cells to exhibit a decreased RNase activity. This indicates that a decrease in the RNase activity exhibited by cells can be used as an index of influence of hydrogen peroxide on the cells.

Example 4

Evaluation of Harmfulness of Hydrogen Peroxide to Cells Using Fluorescently Labeled Double-Stranded RNA—Comparison with Conventional Method This experiment was carried out according to the WST method, which is a conventional technique, using hydrogen peroxide under the same conditions as in Example 3. The viable cell count was determined by the absorbance using a Cell Counting Kit-8 (Dojindo).

For HEK 293 cells ($2\times10^5$ cells/ml in 96 well plate), systems were provided by adding hydrogen peroxide at 0, 0.01, 1, or 100 µM to a cell culture medium based on DMEM (Wako). The cell systems at Hour 2, 4, 6, and 8 were subjected to measurement of the absorbance at 450 nm using a Cell Counting Kit-8 (Dojindo) and a Microplate Reader SH-9000 (Corona Electric) to determine the viable cell count. The experiment was carried out for n=3.

Figure 6:
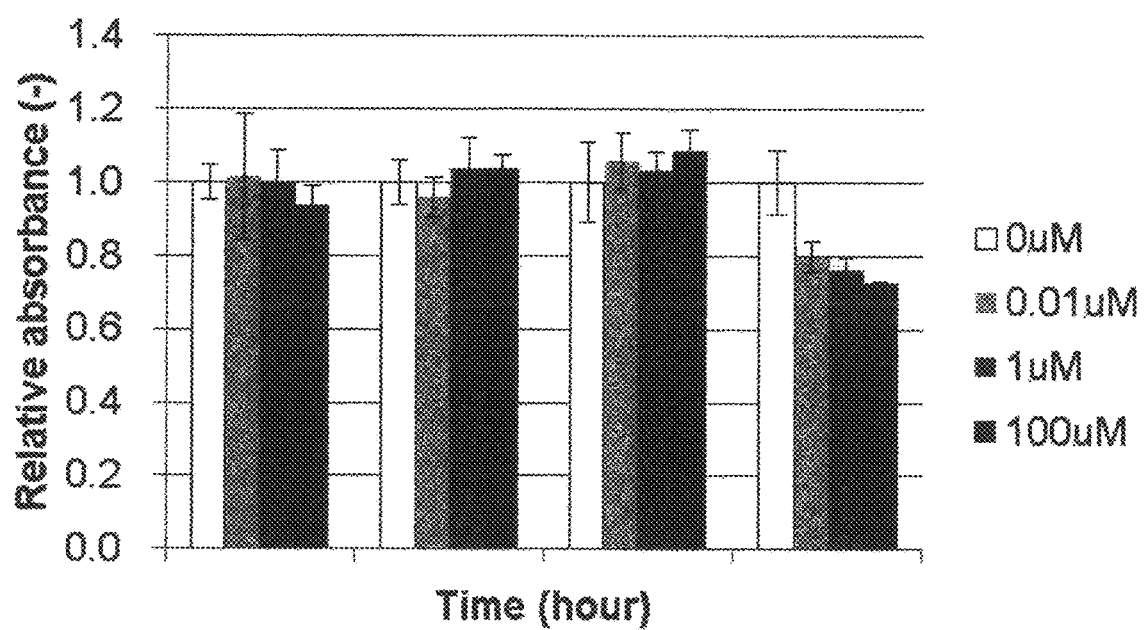
FIG. 6 is a diagram illustrating the result of evaluation of harmfulness of hydrogen peroxide to cells, which evaluation was carried out using a viable cell count determination method according to the conventional WST method.

FIG. 6 shows the result on the relative absorbance value with respect to the value observed for the system to which hydrogen peroxide was not added (0 µM), which is taken as 1. According to the result shown in FIG. 6, a decrease in the absorbance was first found at Hour 8 after the addition of hydrogen peroxide.

That is, it is thought that, in the conventional method, the measurement by the Cell Counting Kit-8 (Dojindo) became possible when the cell death occurred at Hour 8. Thus, it was found, as shown in Example 3, that harmfulness of a chemical substance can be evaluated more quickly by the evaluation of the present invention using a fluorescently labeled double-stranded RNA.

Example 5

Evaluation of Harmfulness of Cisplatin to Cells Using Fluorescently Labeled Double-Stranded RNA In this experiment, Cisplatin was used as a harmful chemical substance to cells, and a fluorescently labeled double-stranded RNA was introduced into mammalian cells. A study was carried out to see whether evaluation of harmfulness of the chemical substance to the cells is possible based on the fluorescence value.

As reaction liquids, systems each containing 50 μL of Opti-MEM (Life Technologies), 1 μL of Lipofectamine 2000 (Life Technologies), 200 nM double-stranded RNA (the same RNA as in Example 1), and 0 ng/ml, 1 ng/ml, 100 ng/ml, or 100 μg/ml Cisplatin (Wako) were provided. After mixing, each reaction liquid was incubated at room temperature for 20 minutes, and then added to HEK 293 cells ($2\times10^5$ cells/ml in 96 well plate), which are human cells. From Hour 0 to Hour 8, fluorescence was measured at 519 nm with excitation at 488 nm using a Microplate Reader SH-9000 (Corona Electric) at one-hour intervals. The experiment was carried out for n=3.

Figure 7:
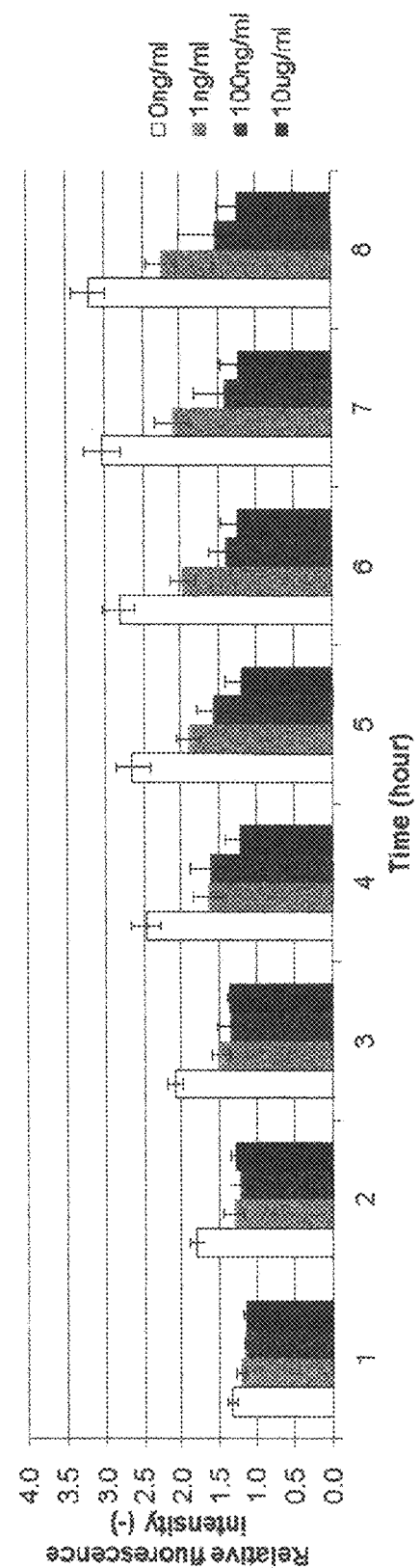
FIG. 7 is a diagram illustrating the result of evaluation of harmfulness of Cisplatin to cells, which evaluation was carried out using the fluorescently labeled double-stranded RNA of the present invention.

The result obtained by dividing the fluorescence values at Hours 1 to 8 by the fluorescence value at Hour 0 is shown in FIG. 7. According to the result shown in FIG. 7, it was found that, while the fluorescence value increases with time in the system to which Cisplatin was not added (0 ng/ml), the increase in the fluorescence value is suppressed in the systems to which Cisplatin was added, and that the suppression is dependent on the Cisplatin concentration. Further, it was found that the changes can be clearly observed in two hours in these systems.

Example 6

Evaluation of Harmfulness of Mercury II Chloride to Cells Using Fluorescently Labeled Double-Stranded RNA In this experiment, Mercury II Chloride was used as a harmful chemical substance to cells, and a fluorescently labeled double-stranded RNA was introduced into mammalian cells. A study was carried out to see whether evaluation of harmfulness of the chemical substance to the cells is possible based on the fluorescence value.

As reaction liquids, systems each containing 50 μL of Opti-MEM (Life Technologies), 1 μL of Lipofectamine 2000 (Life Technologies), 200 nM double-stranded RNA (the same RNA as in Example 1), and 0 ng/ml, 100 ng/ml, 10 μg/ml, or 1 mg/ml Mercury II Chloride (Wako) were provided. After mixing, each reaction liquid was incubated at room temperature for 20 minutes, and then added to HEK 293 cells ($2\times10^5$ cells/ml in 96 well plate), which are human cells. From Hour 0 to Hour 8, fluorescence was measured at 519 nm with excitation at 488 nm using a Microplate Reader SH-9000 (Corona Electric) at one-hour intervals. The experiment was carried out for n=3.

Figure 8:
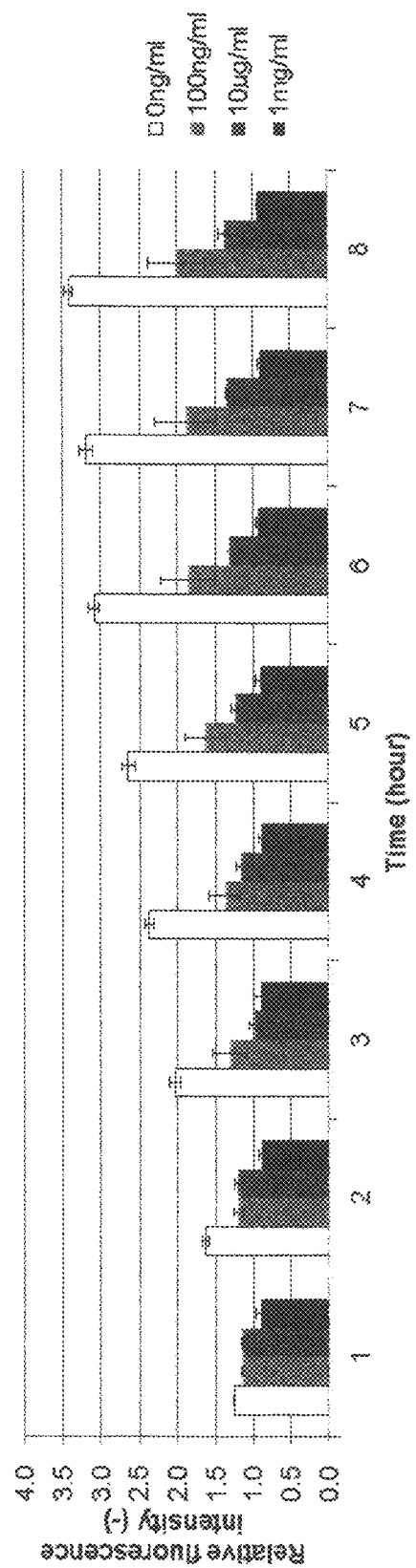
FIG. 8 is a diagram illustrating the result of evaluation of harmfulness of Mercury II Chloride to cells, which evaluation was carried out using the fluorescently labeled double-stranded RNA of the present invention.

The result obtained by dividing the fluorescence values at Hours 1 to 8 by the fluorescence value at Hour 0 is shown in FIG. 8. According to the result shown in FIG. 8, it was found that, while the fluorescence value increases with time in the system to which Mercury II Chloride was not added (0 ng/ml), the increase in the fluorescence value is suppressed in the systems to which Mercury II Chloride was added, and that the suppression is dependent on the Mercury II Chloride concentration. Further, it was found that the changes can be clearly observed in two hours in these systems.

INDUSTRIAL APPLICABILITY

By the method of the present invention, the influence of a harmful chemical substance on the body can be quickly and sensitively evaluated. The present invention can be used in the field of diagnosis, the field of examination, the field of research, and the like related to harmful chemical substances.

---

The invention claimed is:

1. A method for evaluating harmfulness of a chemical substance to a mammalian cell, said method comprising:
   (a) introducing, into a mammalian cell:
      (i) the chemical substance to be evaluated for its harmfulness to the cell, and
      (ii) a double-stranded RNA probe comprising an RNA strand labeled with a fluorescent dye A that emits fluorescence, and an RNA strand labeled with a fluorescent dye B that quenches emission from a fluorescent dye in the vicinity thereof, wherein the fluorescence is quenched in a double-stranded state due to occurrence of fluorescence resonance energy transfer (FRET) between said two kinds of fluorescent dyes; and
   (b) detecting a decrease in the degradation rate of the double-stranded RNA by measuring fluorescence emission, which detection utilizes the principle that,
      (i) in cases where the cell is in the normal state, the double-stranded RNA is degraded by activity of intracellular ribonuclease, the FRET state is canceled, allowing fluorescence emission of the fluorescent dye A, and
      (ii) in cases where the cell is harmfully influenced by the chemical substance, activity of intracellular ribonuclease is suppressed, double-stranded RNA remains undegraded, making the fluorescent dye A remain quenched due to influence of the fluorescent dye B,
   wherein the harmfulness of the chemical substance to the cell is determined when the fluorescent dye A remains quenched.

2. The method according to claim 1, wherein said chemical substance is hydrogen peroxide.

3. The method according to claim 1, wherein said chemical substance is Cisplatin.

4. The method according to claim 1, wherein said chemical substance is Mercury II Chloride.

* * * * *